United States Patent
Dowdeswell et al.

(10) Patent No.: US 6,690,181 B1
(45) Date of Patent: Feb. 10, 2004

(54) IMPEDANCE MEASUREMENTS OF BODILY MATTER

(75) Inventors: Richard Mark Dowdeswell, Cheshire (GB); Peter Alfred Payne, Cheshire (GB); Mohammed El Hassan Amrani, Manchester (GB)

(73) Assignee: Kaiku Ltd., Manchester (GB)

( * ) Notice: Subject to any disclaimer, the term of this patent is extended or adjusted under 35 U.S.C. 154(b) by 0 days.

(21) Appl. No.: 09/869,497

(22) PCT Filed: Jan. 5, 2000

(86) PCT No.: PCT/GB00/00001

§ 371 (c)(1),
(2), (4) Date: Aug. 16, 2001

(87) PCT Pub. No.: WO00/40955

PCT Pub. Date: Jul. 13, 2000

(30) Foreign Application Priority Data

Jan. 5, 1999 (GB) .............................................. 9900103
Aug. 27, 1999 (GB) .............................................. 9920217

(51) Int. Cl.$^7$ .............................................. G01R 27/08
(52) U.S. Cl. ..................................... 324/691; 324/708
(58) Field of Search .................................. 324/318, 322, 324/337, 636, 611, 691, 708; 600/547

(56) References Cited

U.S. PATENT DOCUMENTS

| 4,819,648 A | 4/1989 | Ko | 600/409 |
|---|---|---|---|
| 5,746,214 A | 5/1998 | Brown et al. | 600/547 |
| 6,122,544 A | * 9/2000 | Organ | 600/547 |
| 6,125,297 A | * 9/2000 | Siconolfi | 600/547 |
| 6,151,523 A | * 11/2000 | Rosell Ferrer et al. | 600/547 |
| 6,472,888 B2 | * 10/2002 | Oguma et al. | 324/661 |
| 6,511,851 B1 | * 1/2003 | Payne et al. | 436/149 |

FOREIGN PATENT DOCUMENTS

| EP | 0 865 763 | | 4/1998 | |
| SE | WO 95/34808 | * | 12/1995 | G01N/27/02 |
| WO | 95/34808 | | 12/1995 | |

OTHER PUBLICATIONS

Rigaud B., et al. "Tissue Characterization and Modeling by Electrical Bioimpedance Spectrometry", Proceedings of the Annual International Conference of the IEEE Engineering in Medicine and Biology Society, US, New York, IEEE, vol. 16, pp. 866–867, Nov., 1994.

Thomas B.J., et al. "Bioimpedance Spectrometry in the Determination of Body Water Compartments: Accuracy and Clinical Significance", Applied Radiation and Isotopes, GB, Pergamon Press Ltd., Exeter, vol. 49, No. 5–6, pp. 447–455, May, 1998.

* cited by examiner

Primary Examiner—N. Le
Assistant Examiner—Walter Benson
(74) Attorney, Agent, or Firm—Merchant & Gould P.C.

(57) ABSTRACT

A method and apparatus for generating an impedance spectrum which is characteristic of a sample of bodily matter in a resonant circuit and which may be used to analyse the sample.

28 Claims, 3 Drawing Sheets

IMPEDANCE MEASUREMENTS OF BODILY MATTER

BACKGROUND OF THE INVENTION

1. Field of Invention

The present invention relates to a method and apparatus for generating an impedance spectrum which is characteristic of a sample of bodily matter in a resonant circuit.

2. Related Art

Numerous conditions may give rise to abnormalities in bodily tissue (eg disease, wounding, infection or cancer). In many cases, diagnosis may only be possible by taking a biopsy for ex vivo analysis. As well as being invasive, this method is inefficient and unable to provide rapid online data. In addition, the removal of a biopsy may cause significant discomfort to the subject The electrical impedance spectrum exhibited by a sample or bodily matter is dependent upon its composition. Although bodily matter has previously been analysed by multi-frequency ac impedance measurements, the circuits used were not resonant. For example, it is known to use electrical impedance measurements to determine the status of a part of the body (see inter alia Dijkstra et al, Clinical Applications of Electrical Impedance Tomography, J Med. Eng. and Tech, 17, 3, 98—98).

SUMMARY OF THE INVENTION

The present invention is based on the recognition that the impedance spectrum of a sample of bodily matter which has been made part of a resonant electrical circuit is surprisingly sensitive to the characteristics of the sample of bodily matter and may be used to provide reliable and accurate detection of abnormalities in the sample (eg damaged or infected tissue). Moreover, the present invention is capable of providing information in real time whilst being substantially non-invasive.

Thus viewed from one aspect the present invention provides a method for generating an impedance spectrum which is characteristic of a sample of human or non-human bodily matter (eg tissue), said method comprising the steps of:

applying an electrical signal to the sample of bodily matter at each of a plurality of frequencies in a frequency range including a resonant frequency; and measuring an impedance quantity at each of the plurality of frequencies in the frequency range whereby to generate the impedance spectrum.

Whilst not wishing to be bound by any theoretical consideration, it is nonetheless noted that an impedance quantity ($Z^+$) reflects the response of a sample of bodily matter (eg tissue) to an alternating electric field stimulus and may be considered as a type of transfer function expressing the ratio of the output voltage to input current. This transfer function is related to the composition of the sample of bodily matter being tested The impedance quantity may be considered equivalent to resistance (R) which is measured using direct current. However, in the frequency domain it is a complex number having both a real and an imaginary component expressed by:

$$Z^+ = R + jX$$

(where X is the reactance which is a function of frequency and $j = \sqrt{-1}$). The resonant frequency is that frequency at which reactance is zero and may be regarded as the frequency at which the inductive and capacitive contributions to the reactance cancel out.

Impedance quantities which may be measured in accordance with the invention include the reactance (X) and the phase angle (θ) which are by definition zero at the resonant frequency. A preferred impedance quantity is the dissipation factor (DF) defined as:

$$DF = R/X$$

DF is a measure of the energy dissipated in a circuit by the resistive heating relative to the energy stored in a circuit by capacitive and inductive mechanisms. DF reaches a maximum as X reaches zero (ie as the resonant frequency is reached)

In one embodiment of the invention, the electrical signal is a time varying electrical signal. Preferably, the time varying electrical signal is an alternating current (ac) signal.

The measurement of the impedance quantity may comprise a time to frequency domain transformation of the time varying electrical signal. The steps involved in such a measurement will be generally familiar to those skilled in the art (see for example Perturbation Signals for System Identification, ed K Godfrey, Prentice Hill, 1993, UK). The time varying electrical signal may be periodic and may comprise any suitable function or code eg a pseudo random binary sequence (PRBS), a Golay code, a Walsh function, a Huffman sequence or any other suitable coded sequence. Other suitable signals, codes or methodologies such as white Gaussian noise or wavelet analysis may be employed and will be generally familiar to those skilled in the art (see for example Signal Processing Methods for Audio Images and Telecommunications, ed P M Clarkson and H Stork, Academic Press, London, 1995).

The electrical signal may be applied by at least two electrodes. The electrodes may be in direct or indirect electrical contact With the sample of bodily matter. For example, an insulating layer may be placed over one or more of the electrodes so that the electrodes are in indirect electrical contact with the sample of bodily matter.

In a preferred embodiment of the method of the invention, the electrical signal may be applied by one or more microelectrodes of the type generally or specifically disclosed in WO-A-99/60392 (Farfield Sensors Limited) or specifically claimed therein.

Alternatively, the electrical signal may be applied via at least two windings. The windings may be in direct or indirect electrical contact with the sample of bodily matter.

A means for varying the frequency of the applied electrical signal may be used to apply the electrical signal at a plurality of frequencies in a range including the resonant frequency. For example, at least one inductor or one or more quartz crystal resonators may be used. Conveniently, the means for varying the frequency of the applied electrical signal ensures that the resonant frequency is below about 1 MHz. At such a resonant frequency, problems associated with instrumentation and digitisation are generally reduced.

In a preferred embodiment, the method of the invention comprises the step of comparing the impedance spectrum of an abnormal sample of bodily matter with the impedance spectrum of a normal (ie healthy) sample of bodily matter to deduce the relative characteristics of the normal and the abnormal sample. The term "abnormal sample of bodily matter" may include inter alia cancerous, scarred, infected or diseased tissue.

For example, the impedance spectra may be compared to deduce a shift in the resonant frequency or a difference in the magnitude of the impedance quantity at or near to the resonant frequency. In turn, the relative characteristics of the abnormal and normal sample of tissue may be deduced in a further step.

The method of the invention may be used to detect abnormalities in normal bodily tissue. For example, the method may be advantageously used to detect abnormalities in external bodily tissue including inter alia skin abnormalities, tooth decay, gum disease or cancerous growths. However the method may equally be used on interior bodily tissue to detect abnormalities such as bone abnormalities or cancerous tissue.

In a preferred embodiment, the method of the invention comprises the following steps:

applying a first electrical signal to a first sample of bodily matter at each of a plurality of frequencies in a first frequency range including a resonant frequency;

measuring an impedance quantity at each of the plurality of frequencies in the first frequency range whereby to generate an impedance spectrum of the first sample;

applying a second electrical signal to a second sample of bodily matter at each of a plurality of frequencies in a second frequency range including a resonant frequency;

measuring an impedance quantity at each of the plurality of frequencies in the second frequency range whereby to generate an impedance spectrum of the second sample;

comparing the impedance spectrum of the first sample and the impedance spectrum of the second sample; and deducing the relative characteristics of the first and the second sample of bodily matter.

By way of example, the first sample may be a normal sample of bodily matter (eg healthy tissue) and the second sample may be an abnormal sample of bodily matter. The step of comparing may comprise calculating the shift in resonant frequency between the normal sample of bodily matter and the abnormal sample of bodily matter.

The sensitivity of the method of the invention is such that the shift in the resonant frequency between a sample of normal and a sample of abnormal bodily matter may be significant and may be a downward or an upward shift. For example, a downward shift in resonant frequency is typically characteristic of a sample of diseased skin vis a vis a sample of normal skin whilst an upward shift in resonant frequency is typically characteristic of a sample of scar tissue vis a vis a sample of normal skin. Typically the shifts are as significant as −90 kHz and +100 kHz respectively.

Alternatively, the step of comparing may comprise calculating a change in the magnitude of the impedance quantity at the resonant frequency. This is useful where the impedance quantity is the dissipation factor.

Viewed from a further aspect the present invention provides an apparatus for generating an impedance spectrum which is characteristic of a sample of human or non-human bodily matter (eg tissue), said apparatus comprising:

electrical signal applying means adapted to apply a time varying electrical signal to the sample of bodily matter at each of a plurality of frequencies in a frequency range including a resonant frequency; and measuring means for measuring an impedance quantity characteristic of the sample of bodily matter at each of the plurality of frequencies in the frequency range whereby to generate the impedance spectrum.

In an embodiment of the apparatus of the invention, the electrical signal applying means is capable of applying an ac signal of variable frequency.

In an embodiment of the apparatus of the invention, the electrical signal applying means is capable of applying a time varying electrical signal which is periodic.

The electrical signal applying means may be adapted for use ex vivo or in vivo (externally or internally) as required. The electrical signal applying means may be capable of being positioned in direct or indirect electrical contact with the bodily matter.

The electrical signal applying means may comprise a means for varying tie frequency of the electrical signal to apply the electrical signal at a plurality of frequencies in a range including the resonant frequency. For example, the apparatus may further comprise at least one inductor or at least one quartz crystal resonator. Conveniently, the means for varying the frequency of the electrical signal is arranged so that the resonant frequency is below about 1 MHz. At such a resonant frequency, problems associated with instrumentation and digitisation are generally reduced.

The electrical signal applying means may comprise at least two electrodes. The electrodes may be capable of being positioned in direct or indirect electrical contact with the bodily matter. For example, one or more of the electrodes may comprise an outer insulating layer so that the electrodes are capable of being positioned in indirect electrical contact with the sample of bodily matter.

Numerous electrode materials, sizes and configurations are suitable (as desired) for the preferred embodiment. Generally, the configuration and material may be tailored to the end use. For example, planar electrodes may be used where the sample of bodily matter comprises the skin. Such planar electrodes may be rectangular or half ring configurations as desired. Multiple electrode arrangements may be used where desired. Modulation of the applied electrical field strength is possible to find the optimum working field strength or to provide additional information on the tissue sample.

In a preferred embodiment of the apparatus of the invention, the electrical signal applying means comprises one or more microelectrodes of the type generally or specifically disclosed in WO-A-99/60392 (Farfield Sensors Limited) or specifically claimed therein.

The electrical signal applying means may comprise at least two windings. The windings may be capable of being positioned in direct or indirect electrical contact with the bodily matter. For example, the windings may be potted in a casing of an inert material. This embodiment acts in a similar manner to a transformer ie wherein one winding is energised as a primary winding and drives a second winding which acts as a secondary winding. A current may be induced in the secondary winding with an efficiency which depends on the impedance of the medium between the primary and secondary windings.

In an embodiment of the invention, the electrical signal applying means comprises a probe adapted to be inserted into a bodily cavity and to enable measurement of the impedance spectrum characteristic of the surrounding tissue. The probe may be useful in internal use eg in the detection of cancer (eg cervical cancer). The probe may comprise one or more suitably shaped electrodes (eg needle electrodes) insertable into the bodily cavity.

In an embodiment of the apparatus of the invention, the measuring means may comprise an impedance analyser.

In an embodiment of the apparatus of the invention, the measuring means may be capable of performing a time to frequency domain transformation of the time varying electrical signal.

Viewed from a yet further aspect the present invention provides the use of an apparatus as hereinbefore defined for generating an impedance spectrum at each of a plurality of frequencies in a frequency range including a resonant frequency which is characteristic of a sample of human or non-human bodily matter. Preferably the sample is an exterior part of the human or non-human body (eg the skin).

Viewed from a yet still further aspect the present invention provides a kit of parts suitable for generating an impedance spectrum at each of a plurality of frequencies in a frequency range including a resonant frequency which is characteristic of a sample of human or non-human bodily matter, said kit comprising:

at least two electrodes for applying alternating current to the sample of bodily matter;

an inductor; and an impedance analyser capable of measuring an impedance quantity at each of the plurality of frequencies in the frequency range including the resonant frequency whereby to generate the impedance spectrum.

BRIEF DESCRIPTION OF THE DRAWINGS

Methods and apparatus in accordance with the invention will now be described in a non-limitative sense with reference to the accompanying Figures in which.

DETAILED DESCRIPTION

Figure 1:
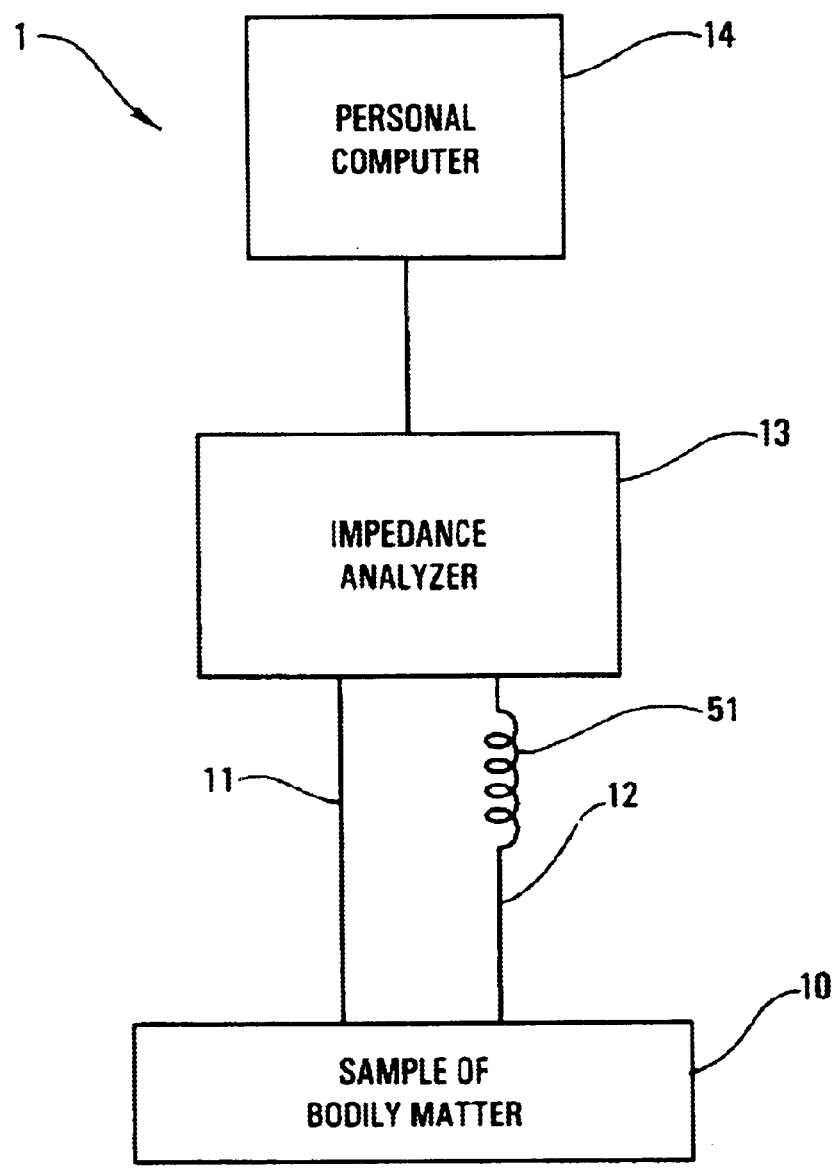
FIG. 1 is a schematic illustration of a first embodiment of an apparatus of the invention.

In a first embodiment of the apparatus of the invention shown schematically in FIG. 1 and designated generally by reference numeral 1, a time varying electrical signal was applied to a sample of bodily matter 10 by two nickel coated steel electrodes 11 and 12 in direct contact therewith. In the first example, the sample of bodily matter was tissue on the back of a human subject's hand which exhibited a small dry scar whose surrounding area was slightly reddened. An inductor 15 was provided in series with electrodes 11 and 12 to ensure that the circuit was capable of resonating. The value of the inductor 15 used (324 mH) was such that the resonant frequency occurred within a tractable range ie at around 1 MHz or less. The applied voltage was 0.2 volts peak to peak which caused minimal discomfort to the subject.

An ac signal of variable frequency was applied and the dissipation factor was measured as a function of the frequency of the applied signal over a frequency range which includes a resonant frequency. The dissipation factor was measured by an impedance analyser 13 (Hewlett Packard 4192A). Data were transferred to a personal computer 14 for further analysis.

Figure 2:
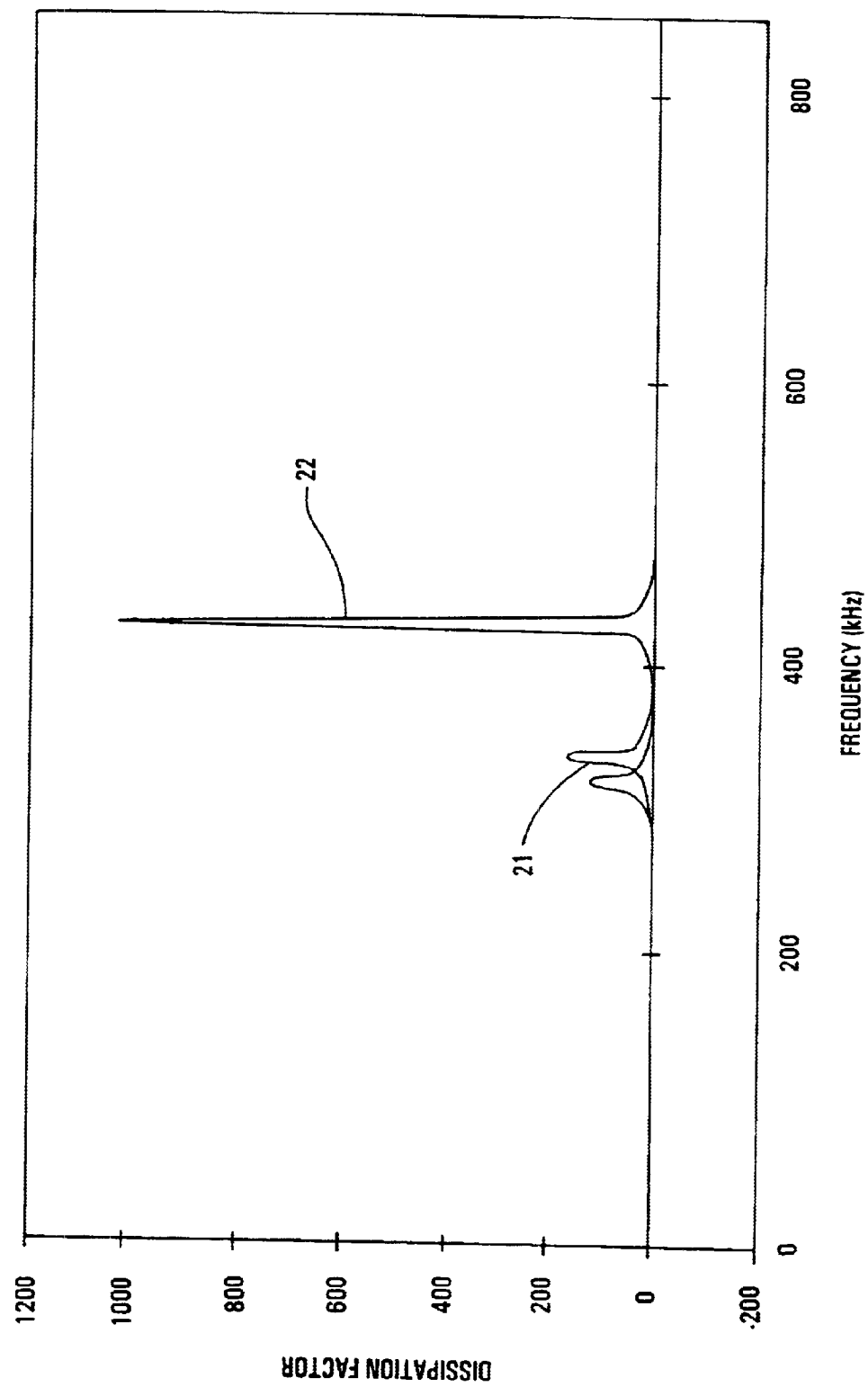
FIG. 2 illustrates dissipation factor as a function of frequency for samples of undamaged skin and scar tissue.

The electrodes 11 and 12 were placed approximately 5 mm from the scar tissue and the dissipation factor spectrum characteristic of the normal sample of tissue was measured at 10 kHz intervals in the range 1 to 800 kHz. This measurement was repeated and the results are shown in FIG. 2 (reference 21). The electrodes 11 and 12 were then placed onto the scar and a similar reading (reference 22) was obtained for the abnormal (scar) tissue also shown in FIG. 2.

It will be seen that the scar tissue and the normal tissue exhibit a significantly different impedance spectrum. The resonant frequency observed for scar tissue is about 100 kHz higher than the resonant frequency of normal tissue. It will also be noted that the upward shift in resonant frequency is accompanied by an apparent increase in the value of the dissipation factor. The maximum calculated value of the dissipation factor is critically dependent upon the value of the reactance as it approaches zero. The calculated value of the maximum dissipation factor is therefore dependent upon the frequency step size and its proximity to the true resonant frequency. The latter is likely to be temperature dependent although given time for any subject to acclimatise to the environment in which the measurements are conducted this may be controlled. Notwithstanding these comments, it is believed that the magnitude of the dissipation factor will provide useful information additional to that provided by the resonant frequency.

Figure 3:
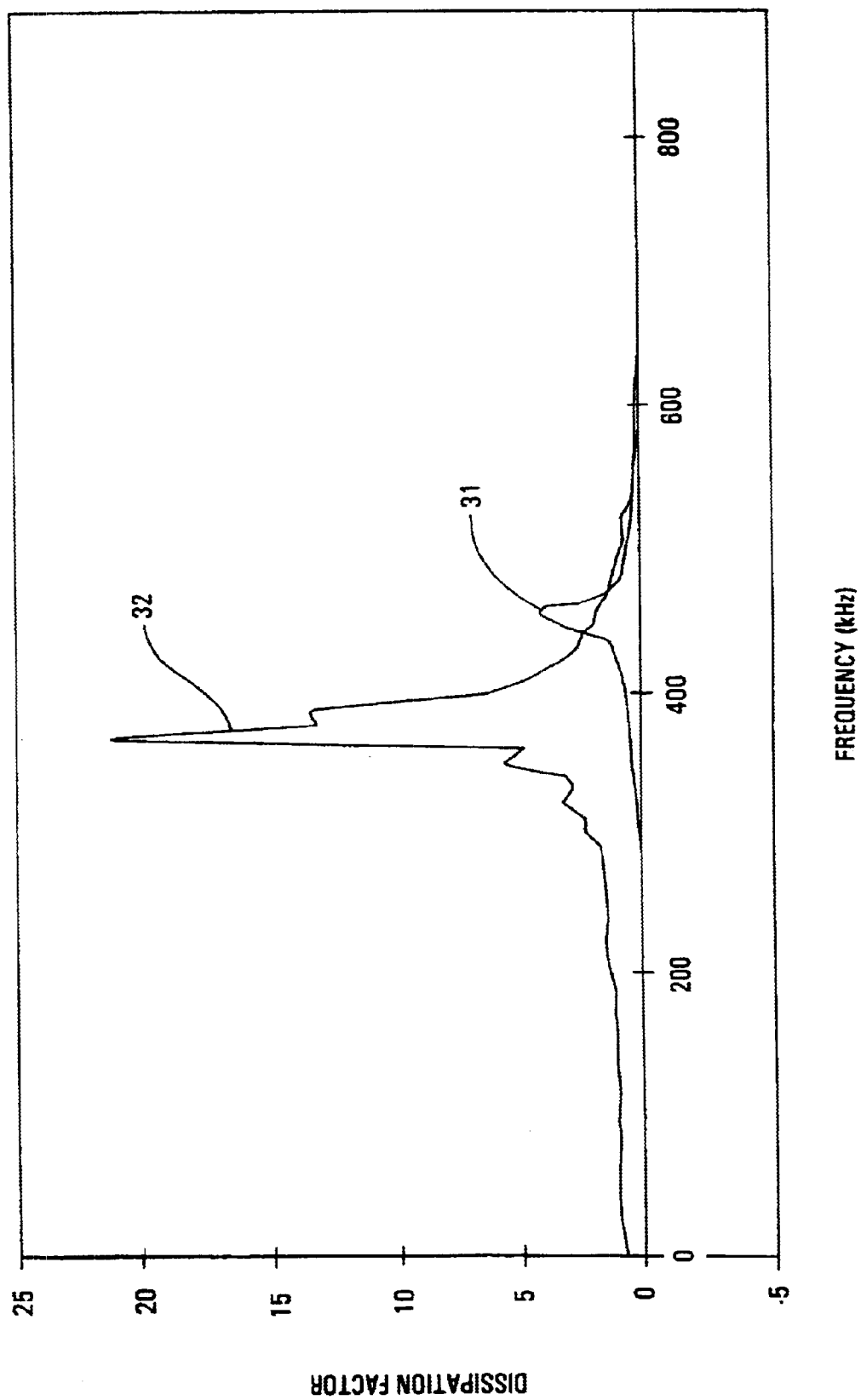
FIG. 3 illustrates dissipation factor as a function of frequency for samples of non-infected and infected skin.

FIG. 3 illustrates the dissipation factor as a function of frequency for a normal and an abnormal sample of skin tissue from the palm of a subject who has an area of diseased skin (dermatitis). Impedance measurements over the range 1–870 kHz were conducted. The normal sample exhibited a resonant frequency at about 460 kHz while the abnormal (diseased) sample was considerably lower at about 370 kHz (references 31 and 32 respectively) It will be noted that the downward shift in resonant frequency characteristic of diseased skin is opposite to the upward shift in resonant frequency characteristic of scar tissue. This leads to the possibility of distinguishing two skin conditions.

What is claimed is:

1. A method for generating an impedance spectrum which is characteristic of a sample of human or non-human bodily matter, said method comprising the steps of:

applying a first electrical signal to a first sample of bodily matter at each of a plurality of frequencies in a first frequency range including a resonant frequency;

measuring an impedance quantity at each of the plurality of frequencies in the first frequency range whereby to generate an impedance spectrum of the first sample;

applying a second electrical signal to a second sample of bodily matter at each of a plurality of frequencies in a second frequency range including a resonant frequency;

measuring an impedance quantity at each of the plurality of frequencies in the second frequency range whereby to generate an impedance spectrum of the second sample;

comparing the impedance spectrum of the first sample and the impedance spectrum of the second sample; and deducing the relative characteristics of the first and second sample of bodily matter.

2. A method as claimed in claim 1 wherein said bodily matter is bodily tissue.

3. A method as claimed in claim 1 wherein said impedance quantity is the dissipation factor.

4. A method as claimed in claim 1 wherein said electrical signal is a time varying electrical signal.

5. A method as claimed in claim 4 wherein the time varying electrical signal is periodic.

6. A method as claimed in claim 4 wherein said time varying electrical signal is an alternating current signal.

7. A method as claimed in claim 4, wherein the measurement of the impedance quantity is a time to frequency domain transformation of the time varying electrical signal.

8. A method as claimed in claim 7 wherein the impedance spectra may be compared to deduce a shift in the resonant frequency or a difference in the magnitude of the impedance quantity at or near to the resonant frequency.

9. A method as claimed in claimed 1 wherein the first sample is a normal sample of bodily matter and the second sample is an abnormal sample of bodily matter.

10. A method as claimed in claim 1 wherein the comparing step comprises: calculating a shift in resonant frequency between the normal sample of bodily matter and the abnormal sample of bodily matter.

11. A method as claimed in claim 10 wherein the shift in resonant frequency is a downward shift in resonant frequency.

12. A method as claimed in claim 10 wherein the shift in resonant frequency is an upward shift in resonant frequency.

13. A method as claimed in claim 10 wherein the shift in resonant frequency is in the range −90 kHz to +100 kHz.

14. A method as claimed in claim 1 wherein the comparing step comprises: calculating a change in magnitude of the impedance quantity at or near to the resonant frequency.

15. A method as claimed in claim 1 conducted in vivo wherein the sample of bodily matter is exterior or interior body tissue.

16. A method as claimed in claim 1 wherein the sample of bodily matter is selected from the group consisting of cancerous, scarred, infected or diseased tissue.

17. An apparatus for generating an impedance spectrum which is characteristic of a sample of human or non-human bodily matter, said apparatus comprising:

electrical signal applying means adapted to apply a time varying electrical signal to the sample of bodily matter at each of a plurality of frequencies in a frequency range including a resonant frequency, wherein the electrical signal applying means includes a means for varying the frequency of the electrical signal to apply the electrical signal at a plurality of frequencies in a range including the resonant frequency; and measuring means for measuring an impedance quantity characteristic of the sample of bodily matter at each of the plurality of frequencies in the frequency range whereby to generate the impedance spectrum, wherein the means for varying the frequency of the electrical signal comprises at least one inductor or at least one quartz crystal resonator.

18. An apparatus as claimed in claim 17 wherein the electrical signal applying means is capable of applying a time varying electrical signal which is periodic.

19. An apparatus as claimed in claim 17 wherein the electrical signal applying means is adapted for use ex vivo or in vivo (externally or internally).

20. An apparatus as claimed in claim 17 wherein the electrical signal applying means is capable of being positioned in direct or indirect electrical contact with the bodily matter.

21. An apparatus as claimed in claim 17 wherein the means for varying the frequency of the electrical signal is arranged so that the resonant frequency is below about 1 MHz.

22. An apparatus as claimed in claim 17 wherein the electrical signal applying means comprises at least two electrodes capable of being positioned in direct or indirect electrical contact with the bodily matter.

23. An apparatus as claimed in claim 17 wherein the electrical signal applying means comprises at least two windings capable of being positioned in direct or indirect electrical contact with the bodily matter.

24. An apparatus as claimed in claim 17 wherein the electrical signal applying means comprises a probe adapted to be inserted into a bodily cavity and to enable measurement of the impedance spectrum characteristic of the surrounding tissue.

25. An apparatus as claimed in claim 17 wherein the measuring means comprises an impedance analyzer.

26. An apparatus as claimed in claim 17 wherein the measuring means is capable of performing a time to frequency domain transformation of the time varying electrical signal.

27. A method for generating an impedance spectrum which is characteristic of a sample of human or non-human bodily matter, said method comprising the steps of:

applying an electrical signal to the sample of bodily matter at each of a plurality of frequencies in a frequency range including a resonant frequency; and measuring an impedance quantity at each of the plurality of frequencies in the frequency range whereby to generate the impedance spectrum, wherein said impedance quantity is the dissipation factor.

28. A method for generating an impedance spectrum which is characteristic of a sample of human or non-human bodily matter, said method comprising the steps of:

applying an electrical signal to the sample of bodily matter at each of a plurality of frequencies in a frequency range including a resonant frequency; and measuring an impedance quantity at each of the plurality of frequencies in the frequency range whereby to generate the impedance spectrum, wherein the measurement of the impedance quantity is a time to frequency domain transformation of the time varying electrical signal.

* * * * *